US005414084A

United States Patent [19]
Willms et al.

[11] Patent Number: 5,414,084
[45] Date of Patent: May 9, 1995

[54] PROCESS FOR THE PREPARATION OF SULFONYLUREAS

[75] Inventors: Lothar Willms, Hillscheid; Stephen Lachhein, Hofheim am Taunus; Günter Schlegel, Liederbach; Heinz Kehne, Hofheim am Taunus, all of Germany

[73] Assignee: Hoechst Aktiengesellschaft, Frankfurt am Main, Germany

[21] Appl. No.: 846,553

[22] Filed: Mar. 5, 1992

[30] Foreign Application Priority Data

Mar. 7, 1991 [DE] Germany ............ 41 07 326.6

[51] Int. Cl.⁶ ............... C07D 239/42; C07D 239/47; C07D 251/46; C07D 25/52
[52] U.S. Cl. ..................... 544/194; 544/320; 544/321; 544/323; 544/332; 544/211; 544/196; 544/197; 544/205; 544/208
[58] Field of Search ............. 544/194, 211, 196, 197, 544/205, 208, 320, 321, 323, 332

[56] References Cited

U.S. PATENT DOCUMENTS

| | | | |
|---|---|---|---|
| 3,931,277 | 1/1976 | Lohaus et al. | 260/465 D |
| 4,191,553 | 3/1980 | Reap | 72/92 |
| 4,600,792 | 7/1986 | Shiokawa et al. | 560/12 |
| 4,601,747 | 7/1986 | Willms et al. | 71/92 |

FOREIGN PATENT DOCUMENTS

| | | |
|---|---|---|
| 2257240 | 5/1974 | European Pat. Off. . |
| 0131258 | 1/1985 | European Pat. Off. . |
| 0158248 | 10/1985 | European Pat. Off. . |
| 0342569 | 11/1989 | European Pat. Off. . |
| 0353641 | 2/1990 | European Pat. Off. . |
| 0409114 | 1/1991 | European Pat. Off. . |
| 89/3643 | 11/1989 | South Africa . |

OTHER PUBLICATIONS

M. I. R. Hedayatullah et al., *Phosphorus, Sulfur and Silicon,* 1991, vol. 61, pp. 19–25.
R. Graf, *Chemische Berichte,* vol. 96, pp. 56–67 (1963).

*Primary Examiner*—John M. Ford
*Attorney, Agent, or Firm*—Curtis, Morris & Safford

[57] ABSTRACT

Herbicidal sulfonylureas of the formula I, $$R^1-X-\underset{\underset{O}{\|}}{\overset{\overset{O}{\|}}{S}}-\underset{R^6}{N}-\underset{\underset{O}{\|}}{\overset{\overset{O}{\|}}{C}}-\underset{R^5}{N}-\!\!\!\!\!\!\!\!\!\!\!\!\!\!\!\!\!\!\!\!\!\!\!\!\begin{array}{c}N=\!\!\!\!\!\!\!\!\!\!\!\!\!\!\!\!\!\!\!\!\!\!<\!\!\!R^3\\Y\\N=\!\!\!\!\!\!\!\!\!\!\!\!\!\!\!\!\!\!\!\!\!\!<\!\!\!R^4\end{array} \quad (I)$$

in which X is $-O-$, $-O-NR^2-$ or $-SO_2-NR^2-$,
Y is $-N-$ or CH,
$R^1$ is (substituted) alkyl, (substituted) alkenyl or (substituted) alkynyl, or else, where X=O, (substituted) phenyl,
$R^2$ is H, alkyl, alkenyl, alkynyl or cycloalkyl,
$R^3$, $R^4$ are H, (substituted) alkyl or (substituted) alkoxy, halogen, alkylthio, alkylamino or dialkylamino and
$R^5$, $R^6$ are H or alkyl, and their salts with acids or bases,
are prepared by reacting compounds of the formula II $$R^1-X-\underset{\underset{O}{\|}}{\overset{\overset{O}{\|}}{S}}-\underset{R^6}{N}-\underset{\underset{O}{\|}}{\overset{\overset{O}{\|}}{C}}-X-R^1 \quad (II)$$

with compounds of the formula III $$HN-\!\!\!\!\!\!\!\!\!\!\!\!\!\!\!\!\!\!\!\!\!\!\!\!\!\!\!\!\!\!\!\!\!\!\!\!\!\!\!\!\!\!\!\begin{array}{c}N=\!\!\!\!\!\!\!\!\!\!\!\!\!\!\!\!\!\!\!\!\!\!<\!\!\!R^3\\Y\\N=\!\!\!\!\!\!\!\!\!\!\!\!\!\!\!\!\!\!\!\!\!\!<\!\!\!R^4\end{array} \quad (III)$$

with $R^5$ on the HN.

6 Claims, No Drawings

PROCESS FOR THE PREPARATION OF SULFONYLUREAS

The invention relates to processes for the preparation of herbicides selected from the group comprising the heterocyclically substituted sulfonylureas, especially the compounds of formula I

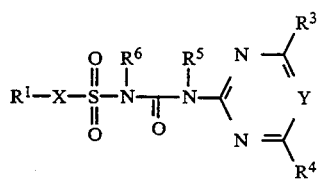 (I)

in which
- X is oxygen, —O—NR$^2$— or —SO$_2$—NR$^2$—, the O or SO$_2$ of the two last-mentioned divalent groups being directly bound to R$^x$,
- Y is nitrogen or CH,
- R$^1$ is (C$_1$–C$_6$)-alkyl, (C$_2$–C$_6$)-alkenyl or (C$_2$–C$_6$)-alkynyl, each of said 3 radicals being unsubstituted or mono- or polysubstituted by radicals selected from the group comprising halogen, (C$_1$–C$_4$)-alkoxy and (C$_1$–C$_4$)-alkoxycarbonyl, or, where X=oxygen, is alternatively phenyl which is unsubstituted or substituted by one or more radicals selected from the group comprising halogen, nitro, (C$_1$–C$_4$)-alkyl, (C$_1$–C$_4$)-haloalkyl, (C$_1$–C$_4$)-alkoxy, (C$_1$–C$_4$)-haloalkoxy or (C$_1$–C$_4$)-alkoxycarbonyl,
- R$^2$ is hydrogen, (C$_1$–C$_6$)-alkyl, (C$_2$–C$_6$)-alkenyl, (C$_2$–C$_6$)-alkynyl or (C$_3$–C$_6$)-cycloalkyl,
- R$^3$, R$^4$ are independently of each other, hydrogen, (C$_1$–C$_4$)-alkyl or (C$_1$–C$_4$)-alkoxy, each of the last-mentioned two radicals being unsubstituted or mono- or polysubstituted by radicals selected from the group comprising halogen, alkoxy and alkylthio, or halogen, (C$_1$–C$_4$)-alkylthio, (C$_1$–C$_4$)-alkylamino or di[(C$_1$–C$_4$)-alkyl]amino and
- R$^5$, R$^6$ are independently of each other, hydrogen or (C$_1$–C$_4$)-alkyl, and their physiologically tolerated salts with acids, or, where at least one of the R$^5$ and R$^6$ radicals is hydrogen, with bases.

Compounds of the formula I are known and are used as crop protection agents having herbicidal activity; see EP-A-0131258 (U.S. Pat. No. 4,601,747), EP-A-0342569 (ZA-A-89/3643) and EP-A-4163 (U.S. Pat. No. 4,191,553). Some processes are also cited or described therein, according to which compounds of the formula I can be prepared.

The known processes have the disadvantage of relatively low yields of at most about 65-70%. As a result, comparatively large amounts of impurities and by-products are produced, which, for application on a commercial scale, represent waste which must be expensively disposed of, for example by means of incineration. The known processes are therefore unfavorable from the ecological and also the economic point of view for carrying out on an industrial, commercial scale. Moreover, at such a low yield, a drastic loss of the starting materials used occurs, which reduces the economic efficiency of the processes.

A new process has now been found by which the compounds of the formula I can be prepared in surprisingly high yield and purity, and which is suitable for carrying out on a large industrial scale.

The present invention relates to a process for the preparation of said compounds of the formula I or their salts, which comprises reacting compounds of the formula II,

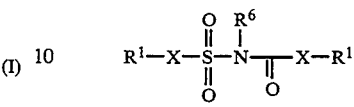 (II)

in which R$^1$, R$^6$ and X are defined as in formula I, with compounds of the formula III,

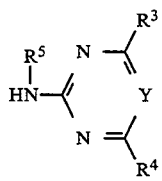 (III)

in which R$^3$, R$^4$, R$^5$ and Y are defined as in formula I.

In the formulae mentioned, alkyl is straight-chain or branched alkyl; this applies correspondingly to the hydrocarbon moiety in the other radicals, such as alkoxy, haloalkyl, haloalkoxy, alkylcarbonyl, alkylamino, alkenyl, alkynyl, alkylsulfonyl etc. Halogen is fluorine, chlorine, bromine or iodine, preferably fluorine, chlorine or bromine. Haloalkyl is alkyl which has been substituted by one or more halogen atoms; this applies correspondingly to haloalkoxy.

Among the processes according to the invention for the preparation of compounds of the formula I, those in which R$^1$X is N-(C$_1$–C$_6$)-alkylsulfonyl-N-(C$_1$–C$_3$)-alkylamino or (C$_1$–C$_4$)-alkoxyphenoxy, R$^3$ and R$^4$ are, independently of each other, (C$_1$–C$_2$)-alkyl or (C$_1$–C$_2$)-alkoxy, R$^5$ is hydrogen and R$^6$ is hydrogen or methyl are of particular interest. Preferably in this case R$^1$X is N-[(C$_1$–C$_3$)-alkylsulfonyl]-N-[(C$_1$–C$_2$)-alkyl]amino, in particular N-(methylsulfonyl)-N-(methyl)amino, N-(methylsulfonyl)-N-(ethyl)amino, N-(ethylsulfonyl)-N-(methyl)amino or N-(ethylsulfonyl)-N-(ethyl)amino, or (C$_1$–C$_3$)-alkoxyphenoxy, in particular 2-methoxyphenoxy, 2-ethoxyphenoxy, 2-n-propoxyphenoxy or 2-isopropoxyphenoxy, and R$^3$ and R$^4$ are, independently of each other, (C$_1$–C$_2$)-alkyl or (C$_1$–C$_2$)-alkoxy, in particular methyl or methoxy, and R$^5$ and R$^6$ are each hydrogen or methyl.

The yields from the process according to the invention are comparatively high, for example 95% of theory and above, the purities of the resulting sulfonylureas of the formula I often being greater than 95% by weight.

The process according to the invention is generally carried out in the presence of inorganic or organic solvents which are inert under the reaction conditions, or mixtures thereof. Inert organic solvents are suitable solvents, but so are water and aqueous organic solvents.

Examples of suitable solvents are aliphatic or aromatic, halogenated or nonhalogenated hydrocarbons, aprotic polar organic solvents, such as dialkylalkanoylamides, dialkyl sulfoxides, polyalkylene glycol dialkyl ethers, N-alkylated cyclic amides and nitriles and also mixtures of said solvents.

Preference is given to solvents such as for example toluene, xylene, chlorobenzene, 1,2-dichloroethane, dimethylformamide, dimethyl sulfoxide, di-, tri- or tetraethylene glycol dialkyl ethers, in particular the dimethyl or diethyl ethers, N-methylpyrrolidone, acetonitrile or alternatively mixtures of two or more of said solvents.

However, the process according to the invention can also be carried out in an aqueous medium, for example a purely aqueous medium.

It is generally advantageous to use the compound of the formula II in an equimolar ratio to the compound of the formula III, or in a slight excess. Preference is given to a molar ratio for II:III of 1:1 to 1.2:1, in particular 1:1 to 1.1:1.

The reaction temperatures are preferably from 0° C. to the boiling point of the solvent used, in particular from room temperature (for example 20° C.) to 110° C.

An advantage of the process according to the invention is that the compound of the formula IV, eliminated from compounds of the formula II, $$R^1\text{—}X\text{—}H \quad (IV)$$

in which $R^1$ and X are defined as above, can be quantitatively recycled in the course of carrying out the process according to the invention and, with subsequent syntheses to give the compounds of the formula II, can be directly reused. If required, prior to recycling, the compounds of the formula IV can be purified, for example in a simple manner by distillation.

A further advantage of this process is the avoidance of the use of compounds of the formula V,

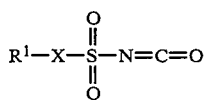

(V)

which are used in conventional processes for the preparation of compounds of the formula I and which are formed as intermediates in these cases at the conventional reaction temperatures of above 110° C. However, under these conventional conditions, the isocyanates of the formula V can be highly thermally labile and partially decompose, which is reflected in low yields (see EP-A-0131258 (U.S. Pat. No. 4,601,747), DE-A-2257240 (U.S. Pat. No. 3,931,277), G. Lohaus, Chem. Ber. 105, 2791-2799 (1972)).

An additional advantage of the process according to the invention is that the solvents can be recycled in almost quantitative yield, as the products of the formula I precipitate as sparingly soluble compounds from the reaction medium in high purity and yield. The solvents can subsequently be purified, for example by distillation, and then reintroduced into the process.

Some of the starting compounds of the formulae II and III, required for the preparation of the compounds of the formula I by the process according to the invention, may be prepared by methods known from the literature.

Thus the heterocyclic compounds of the formula III are either commercially available or may be easily prepared by suitable laboratory methods; see for example U.S. Pat. No. 4,310,470; EP-A-0027200; U.S. Pat. No. 4,299,960; M. J. Langermann, C. K. Banks, J. Am. Chem. Soc. 73,3011 (1951).

The compounds of the formula II are novel and can be obtained by analogy with conventional methods (see for example Tietze and Eicher in "Reaktionen und Synthesen" [Reactions and Syntheses], p. 92, Thieme Verlag, Stuttgart 1981) by reaction of the corresponding sulfonamides VI with the corresponding acid chlorides VII,

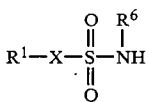

(VI)

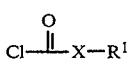

(VII)

which can themselves be synthesized by conventional laboratory methods by reaction of the compound of the formula $R^1\text{—}X\text{—}H$ (said formula IV) and the corresponding amidosulfonyl chlorides of the formula $Cl\text{—}SO_2\text{—}NHR^6$ (giving the product of the formula VI) or phosgene or chloroformate (giving the product of the formula VII) (see for example "Organikum" [Practical Organic Chemistry], 7th edition, p. 539, VEB Deutscher Verlag der Wissenschaften, Berlin 1967).

Furthermore, the compounds of the formula II can be prepared in excellent yield by a new process, which is likewise a subject-matter of the invention. The process comprises reacting compounds of the formula IV with about half the amount of chlorosulfonyl isocyanate:

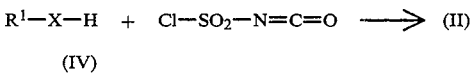

In this case the compounds of the formula IV can be used either as free alcohols, hydroxylamines or amides (depending on the definition of $R^1$ and X), in the presence or absence of an organic or inorganic base, or as a mixture of the free compound IV and a corresponding salt of the compound IV. In the last-mentioned case, preference is given to a mixture of free compound IV with an alkali metal salt of the compound IV, such as the sodium salt or potassium salt, in a molar ratio of about 1:1.

The compound of the formula IV is generally used in a molar ratio to the chlorosulfonyl isocyanate of 1.0:0.5 to 2.0:0.5, preferably 1.0:0.5 to 1.5:0.5.

It is usually appropriate to carry out the reaction in the presence of an inert solvent, the inert organic solvents and types of solvents mentioned in the abovementioned reaction of the compounds of the formulae II and III also being suitable in this case.

The novel process for the production of the compounds II can be carried out in such a manner that the compounds of the formula IV are converted into a 1:1 mixture, based on molar amounts, of the free compound IV and its alkali metal salt using 0.5 mole equivalent of an inorganic base, for example an alkali metal hydroxide or an alkali metal alcoholate, and the mixture is subsequently reacted with 0.5 mole equivalent of chlorosulfonyl isocyanate. Alternatively the free compound IV can be reacted with 0.5 mole equivalent of chlorosulfonyl isocyanate and a base then added, for example an organic base (for example a tertiary amine such as triethylamine) and the reaction continued until consumption of the compound IV. It is also possible in some instances to achieve complete conversion without a base by reaction of the free compound IV with 0.5 mole equivalent of chlorosulfonyl isocyanate with heating of the reaction mixture to the boiling point of the solvent and, if required, distilling off the resulting HCl.

The reaction temperatures for producing the compounds of the formula II depend on the specific compounds of the formula IV and the process variant, and are generally 0° C. to 140° C., preferably 20° C. to 130° C.

The reaction is preferably carried out using a 1:1 mixture of the free compound of the formula IV and an alkali metal salt of the compound of the formula IV. This last process variant results in high yields and, surprisingly, proceeds successfully even at low temperatures suitable for chlorosulfonyl isocyanate of less than 100° C., preferably 50° to 90° C.

In a particularly advantageous development of the invention, the entire reaction sequence for the preparation of a compound of the formula I can be carried out directly, without isolation of the intermediate of the formula II, from the starting compounds of the formula IV and chlorosulfonyl isocyanate, preferably in a one-pot reaction.

The invention therefore also relates to the combination of the part processes mentioned, which comprises
a) reacting the compound of the formula IV and chlorosulfonyl isocyanate in the molar ratio mentioned to give the compound of the formula II and, preferably without isolating the intermediate of the formula II,
b) subsequently reacting the compounds of the formulae II and III to give the compound of the formula I.

The problem-free course of the process according to the invention and the high yield are considered surprising, since the starting product of the formula II contains a plurality of activated, electrophilic and nucleophilic centers. In particular, all of the electrophilic centers can in principle react with the nucleophilic substances of the formula III and thus produce a multiplicity of by-products by fragmentation reactions; cf. Beyer, Lehrbuch der org. Chemie [Textbook of Organic Chemistry], 19th edition, p. 128, Hirzel Verlag Stuttgart, according to which sulfonyl groups and phenoxy groups are very good leaving groups.

The process according to the invention is particularly surprising in the case of compounds of the formula II in which X=—SO$_2$NR$^2$— or —ONR$^2$—, since in this case a transamidation occurs in process step b), which leads virtually quantitatively to the desired product; however, a mixture of the compounds of the formulae II and I in a ratio of about 1:1 was rather to be expected. However, surprisingly, the side reactions and the expected mixture hardly occur at all in the process according to the invention; rather, yields of over 95% of theory and purities of over 95% are generally obtained. Therefore the process according to the invention is a novel, simple, highly reproducible even on a relatively large industrial scale and highly selective process for the production of the compounds of the formula I in virtually quantitative yields. The process can be carried out continuously or discontinuously.

As already briefly mentioned above, it has surprisingly been found that the salts of the compound of the formula IV react at low temperatures in high yields with chlorosulfonyl isocyanate. In a further development of this process variant, a gentle process for the preparation of isocyanates of said formula V has been additionally found, which shows significant advantages in comparison to the conventional process for the preparation of this intermediate for the preparation of the compounds of the formula I. The invention therefore also relates to a process for the preparation of a compound of the formula V

which comprises reacting a salt, preferably an alkali metal salt, of a compound of the formula IV

with chlorosulfonyl isocyanate in a molar ratio of at most 1:1, preferably 1:1 to 0.9:1.

The reaction is advantageously carried out in inert organic solvents, for example those already mentioned above for the other process variants. The reaction temperature is generally less than 100° C., preferably 50° to 90° C. In comparison to conventional processes (see for example DE-A-2257240), the yield of compound of the formula V in the last-mentioned process is improved and thermal decomposition of the isocyanate is avoided. Improvement in the yield of intermediate is simultaneously accompanied by an increase in the economic efficiency of the total process for the preparation of herbicides of the formula (I).

The reaction of IV and chlorosulfonyl isocyanate proceeds with high selectivity at the Cl—S bond and hardly at all at the isocyanate group. This was particularly unexpected since the isocyanate group in chlorosulfonyl isocyanate is normally considered to be more reactive than the C—S bond (see for example DE-A-2257240 and Lohaus, Chem. Ber. 105, 2791–2799 (1972)).

EXAMPLE 1

1-[(N-Methylsulfonyl-N-methyl-amino)-sulfonyl]-3-(4,6-dimethoxy-2-pyrimidyl)urea 32.3 g of 1-[(N-methylsulfonyl-N-methylamino)-sulfonyl]-3-(N-methylsulfonyl-N-methylamino)urea are slurried in 500 ml of chlorobenzene, 15.5 g of 2-amino-4,6-di-methoxypyrimidine are added at 80° C. with stirring, and the mixture is heated for 3 hours at 80° C. After cooling to 20° C., the precipitate is filtered off and washed with 100 ml of chlorobenzene. 36.4 g of the desired product are obtained with a purity of 98.1%, corresponding to a yield of 96.8% of theory. The melting point for the product is 183°–185° C. 5.1 g of N-methylmethanesulfonamide are recovered from the filtrate by distillation, corresponding to a yield of 92.7% of theory.

EXAMPLE 2

1-(2-Ethoxyphenoxysulfonyl)-3-(4,6-dimethoxy-2-pyrimidyl)urea 38.1 g of 2-ethoxyphenyl N-(2-ethoxyphenoxysulfonyl)carbamate are dissolved in 500 ml of toluene, 15.5 g of 2-amino-4,6-dimethoxypyrimidine are added at room temperature, and the mixture is heated for 2 hours at 100° C. After cooling to 30° C., the precipitate is filtered off and washed with 100 ml of toluene. 38.8 g of the desired product are obtained with a purity of 98.8%, corresponding to a yield of 96.4% of theory. The melting point for the product is 147°–149° C. 6.5 g of 2- ethoxyphenol are recovered from the mother liquor by distillation.

The compounds of the formula Ia listed in Table 1 below can be synthesized by analogy with Examples 1 and 2.

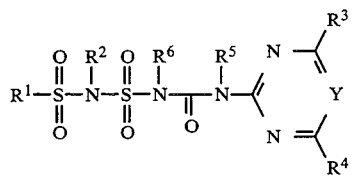

(Ia)

TABLE 1

| | | Compounds of the formula (Ia) | | | | | |
|---|---|---|---|---|---|---|---|
| Ex. | $R^1$ | $R^2$ | $R^3$ | $R^4$ | $R^5$ | $R^6$ | Y | m.p.[°C.] |
| 3 | $CH_3$ | $C_3H_7$ | $CH_3$ | $CH_3$ | H | H | CH | 156–157 |
| 4 | $CH_3$ | $CH(CH_3)_2$ | $CH_3$ | $CH_3$ | H | H | CH | 122–123 |
| 5 | $C_2H_5$ | $C_2H_5$ | $CH_3$ | $CH_3$ | H | H | CH | |
| 6 | $CH_3$ | $CH_3$ | $CH_3$ | $CH_3$ | H | H | CH | |
| 7 | $CH_3$ | $CH_3$ | $CH_3$ | $CH_3$ | H | $CH_3$ | CH | |
| 8 | $C_4H_9$ | $CH_3$ | $CH_3$ | $CH_3$ | H | H | CH | |
| 9 | $CH_3$ | $c$-$C_6H_{11}$ | $CH_3$ | $CH_3$ | H | H | CH | |
| 10 | $C_2H_5$ | $C_2H_5$ | $OCH_3$ | $OCH_3$ | H | H | CH | 148 |
| 11 | $C_2H_5$ | $CH_3$ | $OCH_3$ | $OCH_3$ | H | H | CH | |
| 12 | $C_2H_5$ | $CH_3$ | Cl | $CH_3$ | H | H | CH | 110–112 |
| 13 | $CH_2Cl$ | $CH_3$ | $OCH_3$ | $CH_3$ | H | H | CH | |
| 14 | $CH_3$ | $CH_3$ | $CH_3$ | $OCH_3$ | $CH_3$ | H | N | |
| 15 | $CH_3$ | $C_3H_7$ | $CH_3$ | $OCH_3$ | H | H | N | |
| 16 | $CH_3$ | $CH(CH_3)_2$ | $CH_3$ | $CH_3$ | H | H | N | |
| 17 | $C_2H_5$ | $C_2H_5$ | $CH_3$ | $CH_3$ | H | H | N | |
| 18 | $C_2H_5$ | $CH_3$ | $OCH_3$ | $OCH_3$ | H | H | N | |
| 19 | $C_2H_5$ | $C_2H_5$ | $OCH_3$ | $OCH_3$ | H | H | N | |
| 20 | $C_9H_4$ | $CH_3$ | $CH_3$ | $CH_3$ | H | H | N | |

EXAMPLE 21

(Preparation of compounds of the formula II)

1-[(N-Methylsulfonyl-N-methylamino)-sulfonyl]-3-(N-methylsulfonyl-N-methylamino)urea 109 g of N-methylmethanesulfonamide are dissolved in 1000 ml of chlorobenzene, 20 g of sodium hydroxide are added, and the resulting water of reaction (9 ml) is removed from circulation. 70.0 g of chlorosulfonyl isocyanate are subsequently added dropwise to the reaction solution at 80° C., and the mixture is then heated for 3 hours at 90° C. During the period of the reaction the resulting sodium chloride is precipitated. The reaction mixture is filtered at room temperature and the filter residue is washed free of sodium chloride.

157 g of a product having a purity of 97.2% are obtained, corresponding to a yield of 94.5% of theory. The melting point is 128°–129° C. and is identical to that of a product prepared by an alternative synthesis route.

EXAMPLE 22

(One-pot process)

1-(2-Ethoxyphenoxysulfonyl)-3-(4,6-dimethoxy-2-pyrimidyl)urea 138 g of 2-ethoxyphenol are dissolved in 1000 ml of chlorobenzene, 20 g of sodium hydroxide are added, and the resulting water of reaction (9 ml) is distilled off. 70.5 g of chlorosulfonyl isocyanate are then added dropwise at 50° C. and the mixture is heated for 3 hours at 100° C. During the period of the reaction the resulting sodium chloride is precipitated. The reaction temperature is reduced to 80° C.; 77.5 g of 2-amino-4,6-dimethoxypyrimidine are then added. After stirring for 4 hours at 80° C. the mixture is cooled to room temperature and filtered. The common salt still present is washed from the filtrate with water. There remain 186.5 g of the title sulfonylurea of a purity of 97.8%, corresponding to a yield of 91.6% of theory. The melting point of the product is 146°–148° C. 63.2 g of 2-ethoxyphenol are recovered from the mother liquor by distillation.

EXAMPLE 23

(Preparation of compounds of the formula V)

N-Methanesulfonyl-N-methylaminosulfonyl isocyanate 109 g of N-methylmethanesulfonamide are dissolved in 1000 ml of chlorobenzene, and 180 g of 30% strength sodium methylate solution are added. The mixture is then heated to reflux temperature and the methanol is distilled off. The mixture is subsequently cooled to 50° C. and 141.5 g of chlorosulfonyl isocyanate are slowly added. After addition is completed, the mixture is stirred for 2 h at 80° to 90° C. and the sodium chloride is subsequently filtered off by suction. The crude product solution is freed from the solvent by distillation under reduced pressure. 212 g of crude sulfonyl isocyanate of a purity of 94.3% by weight remain, corresponding to a yield of 93.4% of theory. The refractive index is $n_D^{25} = 1.4768$. The $^1$H-NMR spectrum corresponds to that of a comparison sample prepared by a known synthesis route.

We claim:
1. A process for the preparation of a compound of the formula (I) or a salt thereof,

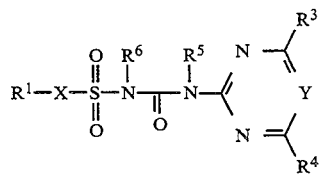

(I)

in which
X is —O—NR$^2$— or SO$_2$—NR$^2$—, the O or SO$_2$ of the two last-mentioned divalent groups being directly bound to R$^1$,
Y is nitrogen or CH,
R$^1$ is (C$_1$–C$_6$)-alkyl, (C$_2$–C$_6$)-alkenyl or (C$_2$–C$_6$)-alkynyl, each of said 3 radicals being unsubstituted or mono- or polysubstituted by radicals selected from the group comprising halogen, $(C_1-C_4)$-alkoxy and $(C_1-C_4)$-alkoxycarbonyl, $R^2$ is hydrogen, $(C_1-C_6)$-alkyl, $(C_2-C_6)$-alkenyl, $(C_2-C_6)$-alkynyl or $(C_3-C_6)$-cycloalkyl, $R^3$, $R^4$ are, independently of each other, hydrogen, $(C_1-C_4)$-alkyl or $(C_1-C_4)$-alkoxy, each of the last-mentioned two radicals being unsubstituted or mono- or polysubstituted by radicals selected from the group comprising halogen, alkoxy and alkylthio, or halogen, $(C_1-C_4)$-alkylthio, $(C_1-C_4)$-alkylamino or di-$[(C_1-C_4)$-alkyl]amino and $R^5$, $R^6$ are, independently of each other, hydrogen or $(C_1-C_4)$-alkyl, or their physiologically tolerated salts with acids, or, where at least one of the $R^5$ and $R^6$ radicals is hydrogen, with bases, which comprises reacting compounds of the formula II,

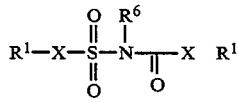

(II)

in which $R^1$, $R^6$ and X are defined as in formula I with compounds of the formula III,

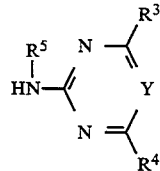

(III)

in which $R^3$, $R^4$, $R^5$ and Y are defined as in formula I.

2. A process as claimed in claim 1, wherein $R^1X$ is $-SO_2-NR^2-$.

3. A process as claimed in claim 2, wherein $R^1X$ is N-$[(C_1-C_3)$-alkylsulfonyl]-N-$[(C_1-C_2)$-alkyl]amino.

4. A process as claimed in claim 3, wherein $R^1X$ is N-(methylsulfonyl)-N-(methyl)amino, N-(methylsulfonyl)-N-(ethyl)amino, N-(ethylsulfonyl)-N-(methyl)amino or N-(ethylsulfonyl)-N-(ethyl)amino.

5. A process as claimed in claim 4, wherein $R^1X$ is N-(methylsulfonyl)-N-(methyl)amino, $R^3$ is methoxy, $R^4$ is methoxy, $R^5$ is H, and $R^6$ is H.

6. A process as claimed in claim 1, wherein the process is carried out in the presence of an inorganic or organic solvent, which is inert under the reaction conditions, or a mixture thereof, and wherein the reaction temperature is in the range of from 0° C. to the boiling point of the solvent used.

* * * * *